United States Patent
Slemon

(10) Patent No.: US 6,677,453 B1
(45) Date of Patent: Jan. 13, 2004

(54) PRODUCTION OF POLYMORPHIC FORMS I AND II OF FINASTERIDE BY COMPLEXATION WITH GROUP I OR II METAL SALTS

(75) Inventor: Clarke Slemon, Montreal (CA)

(73) Assignee: Torcan Chemical LTD, Aurora (CA)

( * ) Notice: Subject to any disclaimer, the term of this patent is extended or adjusted under 35 U.S.C. 154(b) by 0 days.

(21) Appl. No.: 10/111,979

(22) PCT Filed: Nov. 1, 1999

(86) PCT No.: PCT/CA99/01017

§ 371 (c)(1),
(2), (4) Date: Jun. 18, 2002

(87) PCT Pub. No.: WO01/32683

PCT Pub. Date: May 10, 2001

(51) Int. Cl.⁷ .......................... C07D 221/18; C07J 73/00

(52) U.S. Cl. ............................................ 546/77; 546/61

(58) Field of Search ...................................... 546/77, 61

(56) References Cited

U.S. PATENT DOCUMENTS 5,886,184 A * 3/1999 Dolling et al. ................. 546/77

FOREIGN PATENT DOCUMENTS

GB 1 555 968 11/1979

* cited by examiner

Primary Examiner—Charanjit S. Aulakh

(57) ABSTRACT

Polymorphic Form (I) finasteride is prepared by first forming a substantially insoluble complex of finasteride and a Group (I) or Group (II) metal salt, such as lithium bromide, and then dissociating the complex by dissolving away the salt component with water, so as to obtain substantially pure Form (I) polymorphic crystalline finasteride.

17 Claims, 1 Drawing Sheet

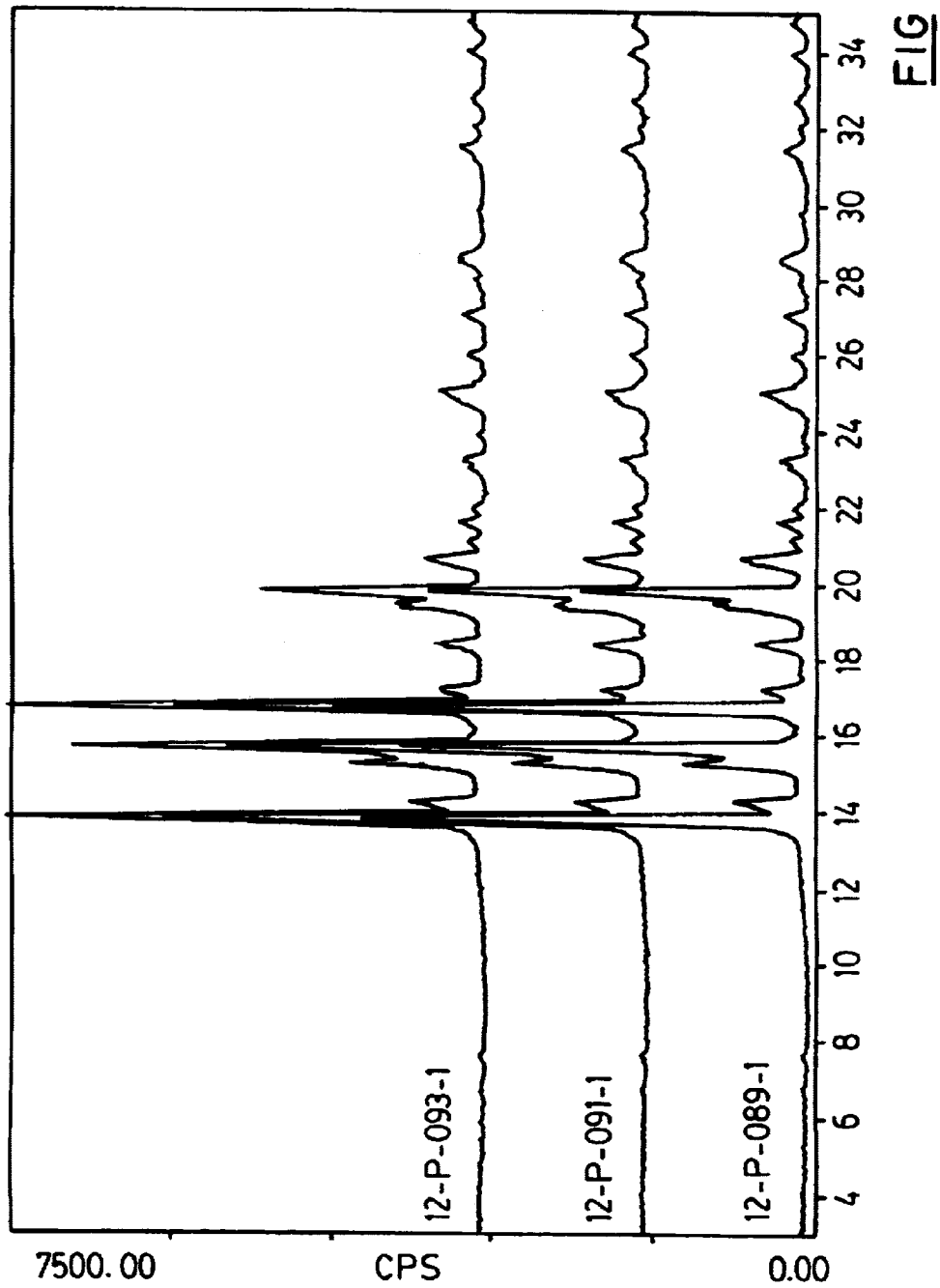

PRODUCTION OF POLYMORPHIC FORMS I AND II OF FINASTERIDE BY COMPLEXATION WITH GROUP I OR II METAL SALTS

This application a 371 of PCT/CA99/01017 filed Nov. 1, 1999, now WO 01/32683

This invention relates to finasteride, a 4-aza-steroid compound which exhibits pharmaceutical activity as an inhibitor of the enzyme testosterone 5-α-reductase, and is useful in the treatment of prostate cancer. More specifically, it relates to processes for preparing finasteride in a specific, polymorphic form.

BACKGROUND OF THE INVENTION

Finasteride is, chemically, (5α, 17β)-N-(1,1-dimethylethyl)-3-oxo-4-aza-androst-1-ene-17-carboxamide, of chemical structural formula:

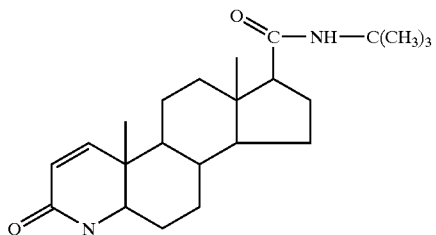

It is reported to be active in inhibiting the activity of the enzyme testosterone-5-α-reductase, which causes reduction of testosterone in the body to dihydrotestosterone, DHT, implicated in the enlargement of the prostate and consequent development of malignant conditions namely prostate cancer. Accordingly, finasteride is prescribed for alleviation of prostate cancer.

Finasteride can exist in two different polymorphic forms, Form I and Form II, which differ from one another in respect of their crystalline structure. The different polymorphic forms can be prepared by control of the crystallization conditions. Finasteride polymorphic Form I is the usual form and is the form which is marketed as the active ingredient of the finasteride drug formulation PROSCAR®. According to Canadian Patent Application 2,103,107 Dolling et al. (equivalent to European patent application 0599376), finasteride polymorphic Form I is characterized by an X-ray powder diffraction pattern having d-spacings of 6.44, 5.69, 5.36, 4.89, 4.55, 4.31, 3.85, 3.59 and 3.14. According to the same Canadian patent, finasteride polymorphic Form II is characterized by an X-ray powder diffraction pattern having d-spacings of 14.09, 10.36, 7.92, 7.18, 6.40, 5.93, 5.66, 5.31, 4.68, 3.90, 3.60 and 3.25.

The preparation of finasteride is described and claimed in U.S. Pat. No. 4,377,584 and further described in U.S. Pat. No. 4,760,071. Other patents which pertain to the preparation of finasteride include Canadian Patent application 2,029,859; U.S. Pat. Nos. 5,084,574 and 5,116,983 and Canadian patent applications 2,049,882 and 2,049,881. All these teach the conversion of a final intermediate to finasteride, which is purified and isolated as a crystalline solid. Although finasteride polymorphs are not mentioned specifically in these items of prior art, the finasteride obtained using them, as a crystalline solid, must be in one or other of the known polymorphic forms, or a mixture of both of them.

Aforementioned Canadian Patent Application 2,103,107 Dolling et al., published May 20, 1994, describes preparations of finasteride and the specific polymorphic Form I and Form II thereof. In particular, it teaches that polymorphic Form I can be prepared by crystallization from a mixture of finasteride in an organic solvent and optionally water, such that the amount of organic solvent and water in the mixture is sufficient to cause the solubility of the non-solvated form of finasteride (Form I) to be exceeded and the non-solvated form of finasteride to be less soluble than any other form of finasteride in the mixture. It also teaches that the polymorphic Form I of finasteride can be prepared by heating the polymorphic Form II of finasteride to at least 25° C. in water or an organic solvent for a sufficient period of time to effect the conversion. The same reference teaches that polymorphic Form II finasteride can be prepared by crystallization from a mixture of finasteride in an organic solvent and water, such that the amount of organic solvent and water in the mixture is sufficient to cause the solubility of the solvated form of finasteride to be exceeded and the solvated form of finasteride to be less soluble than any other form of finasteride in the mixture, followed by recovery of the solid and removal of the solvent therefrom; or by heating polymorphic Form I finasteride to at least to about 150° C. for sufficient time to complete the conversion.

Purifying crude organic compounds by treating with Group I and Group II metal salt in a non-hydroxylic solvent to precipitate metal salt complexes has been described in GB 2094795, U.S. Pat. No. 4,452,994 and U.S. Pat. No. 4,529,811. The hypothesis has been offered that the crystal lattice energy between the very small ion radius of the Group I or Group II metal cation and the much larger ion radius of the chosen anion tends to promote the inclusion of organic substances in the lattice when such substances are capable of helping the solvation of the small cation; but, the actual formation of such complexes cannot be reliably predicted for complex molecules and so must be demonstrated by experiment.

DESCRIPTION OF THE INVENTION

It is an object of the present invention to provide a novel process for preparing finasteride in its pharmaceutically desirable, polymorphic Form I.

It is a further object of the invention to provide novel intermediates useful in preparation of polymorphic Form I finasteride and in other aspects of finasteride preparation.

According to one aspect of the present invention, there is provided a process of preparing polymorphic Form I finasteride, which comprises preparing a finasteride—Group I or Group II metal salt complex, in the presence of a non-hydroxylic solvent, dissociating the complex by addition of acidified water thereto, and recovering the crystalline Form I finasteride so formed.

According to a second aspect of the present invention, there are provided chemical complexes of finasteride and the salt of a Group I or Group II metal, said complexes being dissociable upon addition of acidified water thereto, to yield water-insoluble polymorphic Form I finasteride.

According to a further aspect of the invention, there is provided a process for preparing chemical complexes of finasteride and a Group I or Group II metal salt, which comprises dissolving crude finasteride in a non-hydroxylic, chemically inert, organic solvent, and adding to the solution so formed a salt of a Group I or Group II metal.

The finasteride-metal salt complexes formed in the process of the present invention have been found, by X-ray powder diffraction, to be nearly amorphous solids. Neither the spectral lines of Form I or Form II of finasteride are present in these amorphous solids. When these complexes are dissociated according to the process of the invention, by addition of acidified water thereto, the metal salt is dissolved and the solid which is obtained upon filtration, surprisingly and unpredictably, turns out to be finasteride Form I. The precursor complexes, and any finasteride solvates initially present, as impure substances, do not of course exhibit polymorphic crystalline forms.

Another aspect of the invention is a method of isolating finasteride in substantially pure, polymorphic Form I, from a solution thereof in an organic non-hydroxylic solvent, which comprises adding to said solution a salt of a Group I or Group II metal to form a sparingly soluble complex thereof with finasteride, separating the finasteride complex by filtration, and adding acidified water thereto to break the complex and form substantially pure, isolatable polymorphic Form I finasteride.

Addition of acidified water e.g. water containing about 10% v/v acetic acid, to the amorphous solid complex removes the metal salt by dissolution into the aqueous solution, and catalyses the transformation of the finasteride component, which never dissolves, into polymorphic Form I finasteride in substantially pure condition, which can be filtered, washed and dried.

The Group I or Group II metal salts preferably used In the present invention are lithium salts and calcium salts, and most preferably lithium salts with relatively large anions, for example bromide, iodide, tetrafluoroborate, perchlorate, hexafluorophosphate and the like. Especially preferred is lithium bromide.

In the preparation of the finasteride-metal complexes according to the invention, finasteride in any of its polymorphic forms, as mixtures of polymorphic forms, or as a solvate with an organic solvent, or in impure form, in solution in a non-hydroxylic, nonreactive organic solvent, is dissolved in a non-hydroxylic organic solvent which does not contain complexable functional groups which will interact with the finasteride. In a particular preferred embodiment, the finasteride solution is that resulting from the work-up of the reaction mixture from the chemical synthesis of finasteride, for example by the method of reacting (5α, 17β)-N-(1,1-dimethylethyl)-3-oxo-4-aza-androstan-17-carboxamide with dichlorodicyanoquinone and bistrimethylsilyltrifluoroacetamide in solution in an non-hydroxylic inert organic solvent. The metal salt is added to this solution, and sparingly soluble finasteride-metal salt complex precipitates. This finasteride-metal salt complex can optionally be dried, with or without the application of heat Suitable solvents include hexanes and other aliphatic and cycloaliphatic hydrocarbons, aromatic hydrocarbons such as benzene, toluene, xylenes, halogenated aliphatic hydrocarbons such as methylene chloride and other chlorinated hydrocarbons, ethers such as diethylether, diisopropyl ether and t-butylmethyl ether, and ketones such as methyl isobutyl ketone, and mixtures of two or more mutually compatible such solvents. The quantity of solvent is not critical.

The finasteride-metal salt complexes may be prepared at any suitable temperature at which the chosen solvent remains liquid. The chosen temperature is not critical. Room temperatures are suitable and convenient. Similarly the stoichiometry of the finasteride and the metal salt is not critical, although operating at dose to stoichiometric ratios is economical and avoids waste of reagents.

The complex formation benefits from the presence in the organic solvent solution of a small, catalytic quantity of water or lower ($C_1$–$C_6$) alkanol. This has the effect of increasing the rate of formation of the complex. The catalyst quantity should be chosen so as to be adequate to exert its catalytic, accelerating effect, but not sufficient to compete significantly for the metal salt or to increase significantly the low solubility of the complex. Amounts up to about 1% of Water or lower alkanol are suitable.

BRIEF DESCRIPTION OF THE DRAWING

The attached FIGURE shows three X-ray powder defraction patterns.

EXAMPLES

The invention is illustrated in the following specific examples.

Example 1

Preparation of Finasteride-lithium Bromide Complex

Into a 100 ml r.b. flask equipped with a magnetic stirrer and a nitrogen inert atmosphere was weighted 3.71 gm of finasteride. Methylene chloride (20 ml) was added and the slurry astirred to dissolve the substrate. To the clear light yellow solution was added 0.87 g of anhydrous lithium bromide. The solid was washed down into the reaction with 5 ml of methylene chloride. The slurry was stirred. Within one minute add 1 drop of n-propanol from a disposable pipette. The slurry was stirred overnight with exclusion of moisture under an inert nitrogen atmosphere. The slurry is filtered on a Buchner funnel and the flask and solid washed with 10 ml of methylene chloride. After drying the solid at 50° C. in vacuum the solid complex weighs 4.17 g. The methylene chloride solution contains 0.35 g of nonvolatile residue.

Example 2

Preparation of Finasteride Form I

In a 25 ml r.b. flask equipped with a magnetic stirrer and a static nitrogen purge was placed 0.53 g of finasteride-lithium bromide complex. To this was added 10 ml of 9:1 v/v water/acetic acid and the slurry was stirred for two hours at 50° C. The slurry was cooled to 20–25° C. and filtered. The solid on the filter was washed with water and dried in vacuum at 40–45° C. The solid weighed 0.37 g.

Three different samples of finasteride prepared in three separate experiments according to this Example 2 where analyzed by x-ray powder diffraction, and the single FIGURE of accompanying drawings shows these three x-ray powder diffraction patterns. They are identical to one another, and identify the products as finasteride Form I. Further confirmation of the identity of the product as finasteride Form I was obtained by differential scanning calorimetry.

I claim:

1. A process of preparing polymorphic Form I finasteride, which comprises preparing a finasteride—lithium or calcium salt complex, in the presence of a non-hydroxylic solvent, dissociating the complex by addition of acidified water thereto, and recovering the crystalline Form I finasteride as formed.

2. The process of claim 1 wherein the metal salt of the complex is a lithium salt with a relatively large anion.

3. The process of claim 2 wherein the lithium salt is lithium bromide.

4. The process of claim 1, wherein the acidified water is a water-acetic acid mixture.

5. The process of claim 1 wherein the non-hydroxylic solvent is an aliphatic hydrocarbon, a cycloaliphatic hydrocarbon, a halogenated aliphatic hydrocarbon, an aromatic hydrocarbon, an ether, a ketone or a mixture of two or more compatible such solvents.

6. The process of claim 5 wherein the solvent is methylene chloride.

7. A chemical complex of finasteride and lithium or calcium metal salt, said complex being dissociable upon addition of acidified water thereto, to yield water-insoluble polymorphic Form I finasteride.

8. The complex of claim 7 wherein the metal salt is a lithium salt with a relatively large anion.

9. The complex of claim 8 wherein the metal salt is lithium bromide.

10. A process for preparing a chemical complex of finasteride and a lithium or calcium metal salt, which comprises dissolving crude finasteride in a non-hydroxylic, chemically inert, organic solvent, and adding to the solution so formed a salt of a lithium or calcium metal.

11. The process of claim 10 wherein the salt is a lithium salt with a relatively large anion.

12. The process of claim 11 wherein the salt is lithium bromide.

13. The process of claim 10, catalysed by a catalytic amount of water or lower ($C_1$–$C_6$) alkanol in the reaction medium.

14. A method of isolating finasteride in substantially pure, polymorphic Form I, from a solution thereof in an organic non-hydroxylic solvent, which comprises adding to said solution a salt of a lithium or calcium metal to form a sparingly soluble complex thereof with finasteride, separating the finasteride complex by filtration, and adding acidified water thereto to break the complex and form substantially pure, isolatable polymophic Form I finasteride.

15. The method of claim 14 wherein the salt is a lithium salt with a relatively large anion.

16. The method of claim 15 wherein the salt is lithium bromide.

17. The method of claim 14, wherein the insoluble complex is formed in the presence of a catalytic amount of water or lower ($C_1$–$C_6$) alkanol.

* * * * *